United States Patent
Dickson

(10) Patent No.: US 6,557,548 B1
(45) Date of Patent: May 6, 2003

(54) INFANT BREATHING AID ASSEMBLY

(76) Inventor: Ian A. Dickson, 13 Longford Avenue, Bedfont Feltham Middlesex TW14-9TQ (GB)

( * ) Notice: Subject to any disclaimer, the term of this patent is extended or adjusted under 35 U.S.C. 154(b) by 0 days.

(21) Appl. No.: 09/785,128

(22) Filed: Feb. 16, 2001

(51) Int. Cl.$^7$ .............................................. A61M 15/00
(52) U.S. Cl. ........................ 128/200.24; 128/201.26
(58) Field of Search .................. 128/200.24, 200.16, 128/201.26, 202.16, 203.16, 203.12, 203.26, 203.27, 204.13, 206.29; 606/234, 236; D24/194–198; 215/216, 200, 208, 209, 250

(56) References Cited

U.S. PATENT DOCUMENTS

| | | | |
|---|---|---|---|
| 3,656,647 A * | 4/1972 | Swinn | 215/208 |
| 3,820,690 A * | 6/1974 | Musher | 222/490 |
| 3,860,136 A * | 1/1975 | Romney | 215/222 |
| 3,895,737 A * | 7/1975 | Phillips | 221/82 |
| 4,715,379 A * | 12/1987 | McCormick | 128/360 |
| 4,749,093 A * | 6/1988 | Trick | 215/220 |
| 4,991,729 A * | 2/1991 | Hunter | 215/206 |
| 5,078,734 A * | 1/1992 | Noble | 606/236 |
| 5,146,913 A * | 9/1992 | Khorsandian et al. | 128/200.26 |
| 5,147,053 A * | 9/1992 | Friedenthal | 215/216 |
| 5,176,705 A * | 1/1993 | Noble | 606/236 |
| 5,375,593 A * | 12/1994 | Press | 128/207.18 |
| 5,395,392 A * | 3/1995 | Suhonen | 606/234 |
| 5,514,142 A | 5/1996 | Dean-Homolka | |
| 5,551,582 A * | 9/1996 | Robinson | 215/216 |
| 5,579,933 A * | 12/1996 | Hofmann | 215/220 |
| 5,601,605 A * | 2/1997 | Crowe et al. | 606/236 |
| 5,609,582 A * | 3/1997 | Krutten | 604/247 |
| 5,620,462 A * | 4/1997 | Valenti | 606/234 |
| 5,685,291 A * | 11/1997 | Marsh | 128/200.15 |
| D387,868 S | 12/1997 | Wilburn | |
| 5,699,922 A * | 12/1997 | Harding | 215/208 |
| 5,772,685 A * | 6/1998 | Crowe et al. | 606/236 |
| 5,810,003 A | 9/1998 | Findlater | |
| 5,868,131 A | 2/1999 | Murchie | |
| 5,904,140 A * | 5/1999 | McGoogan | 128/200.24 |
| 5,908,438 A | 6/1999 | Munoz et al. | |
| 5,947,345 A * | 9/1999 | Hofmann | 222/519 |
| 5,979,680 A * | 11/1999 | Farside | 215/216 |
| 5,993,413 A * | 11/1999 | Aaltonen et al. | 604/77 |
| 6,068,649 A * | 5/2000 | Chamberlain | 606/234 |
| 6,110,193 A * | 8/2000 | Chen | 606/234 |
| 6,126,678 A * | 10/2000 | Aaltonen et al. | 606/234 |
| 6,197,044 B1 * | 3/2001 | Clayton | 606/236 |
| 6,203,566 B1 * | 3/2001 | Alanen et al. | 606/234 |
| 6,244,518 B1 * | 6/2001 | Pogue | 239/36 |
| 6,264,678 B1 * | 7/2001 | Landers | 606/236 |
| 6,343,705 B1 * | 2/2002 | Minnette | 215/216 |
| 6,450,352 B1 * | 9/2002 | DeJonge | 215/217 |
| 6,470,882 B1 * | 10/2002 | Newhouse et al. | 128/200.24 |

FOREIGN PATENT DOCUMENTS

| | | | |
|---|---|---|---|
| CH | 679009 A5 | * | 9/1989 |
| GB | 2231497 A | * | 11/1990 |

\* cited by examiner

*Primary Examiner*—Weilun Lo
*Assistant Examiner*—Teena Mitchell

(57) ABSTRACT

An infant breathing aid assembly for administering a vapor of an aromatic substance to a child having trouble breathing. The infant breathing aid assembly includes an oral member for placing in the mouth of the infant. A first end of the oral member has a chamber extending therein toward the second end of the oral member. A face shield is provided for preventing the oral member from being swallowed by the infant. The face shield is preferably mounted on the oral member and positioned generally between the first end of the oral member and the face shield. A vapor emitter is provided that is removably insertable in the chamber of the oral member. The vapor emitter preferably comprises an absorbent member for absorbing an aromatic material. A cover is provided for covering the chamber and allowing passage of the vapors from the absorbent member out of the chamber. The cover is releasably attachable to the first end of the oral member.

20 Claims, 4 Drawing Sheets

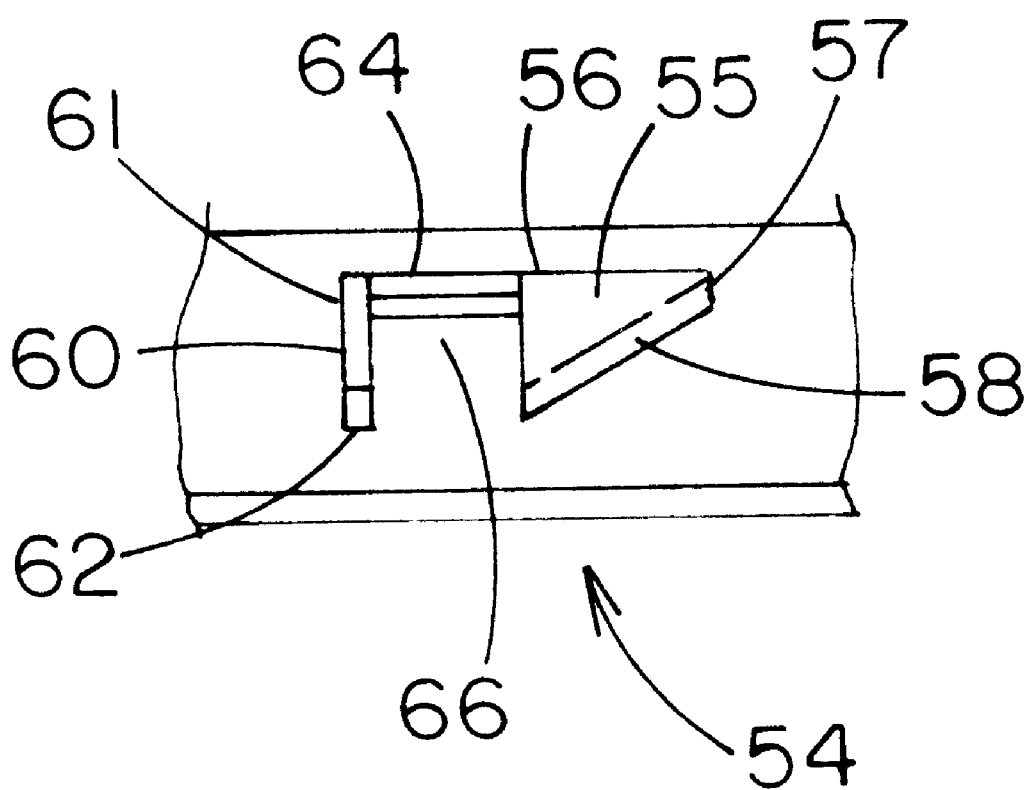

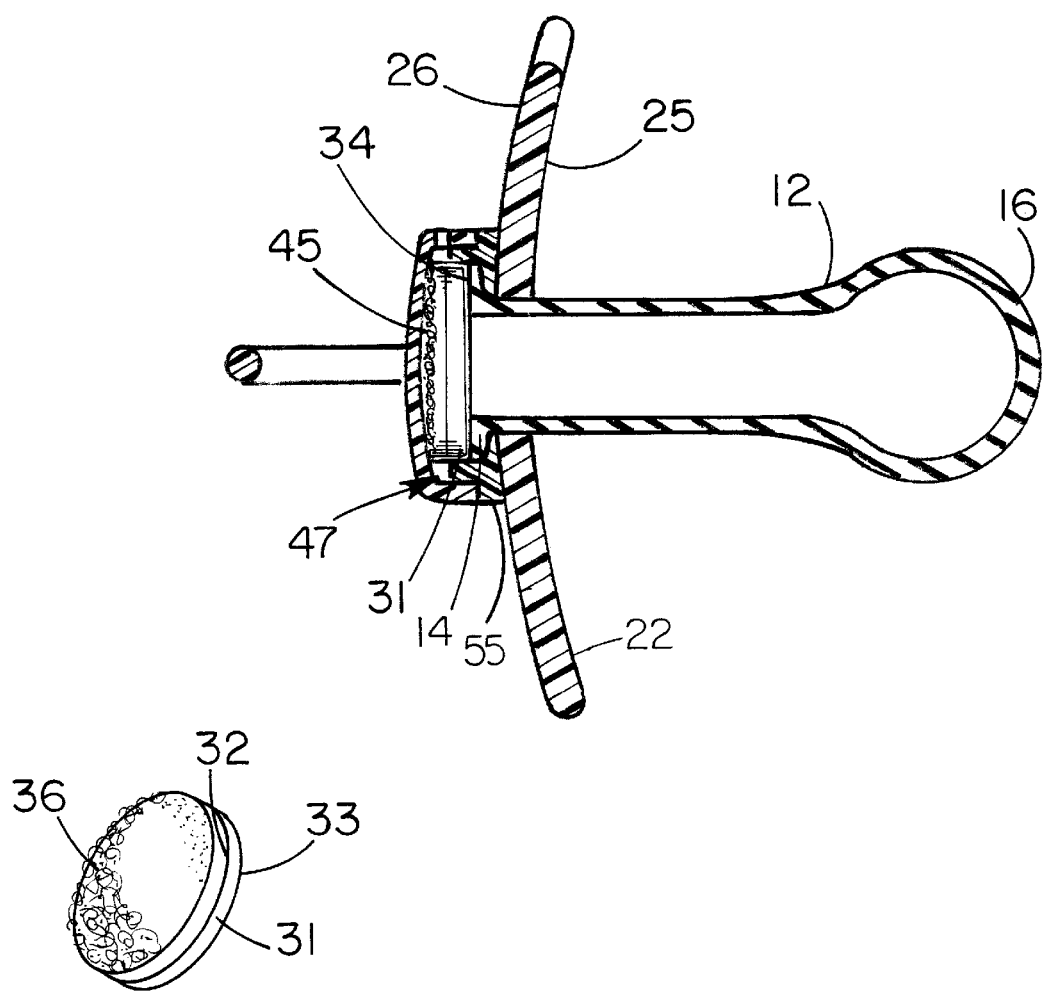

INFANT BREATHING AID ASSEMBLY

BACKGROUND OF THE INVENTION

1. Field of the Invention

The present invention relates to pacifiers and more particularly pertains to a new infant breathing aid assembly for administering a vapor of an aromatic substance to a child having trouble breathing.

2. Description of the Prior Art

The use of pacifiers is known in the prior art. More specifically, pacifiers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,868,131; 5,810,003; 5,514,142; 5,908,438; 5,620,462; and U.S. Pat. No. Des. 387,868.

While these devices fulfill their respective, particular objectives and requirements, the aforementioned patents do not disclose a new infant breathing aid assembly. The inventive device includes an oral member for placing in the mouth of the infant. A first end of the oral member has a chamber extending therein toward the second end of the oral member. A face shield is provided for preventing the oral member from being swallowed by the infant. The face shield is preferably mounted on the oral member and positioned generally between the first end of the oral member and the face shield. A vapor emitter is provided that is removably insertable in the chamber of the oral member. The vapor emitter preferably comprises an absorbent member for absorbing an aromatic material. A cover is provided for covering the chamber and allowing passage of the vapors from the absorbent member out of the chamber. The cover is releasably attachable to the first end of the oral member.

In these respects, the infant breathing aid assembly according to the present invention substantially departs from the conventional concepts and designs of the prior art, and in so doing provides an apparatus primarily developed for the purpose of administering a vapor of an aromatic substance to a child having trouble breathing.

SUMMARY OF THE INVENTION

In view of the foregoing disadvantages inherent in the known types of pacifiers now present in the prior art, the present invention provides a new infant breathing aid assembly construction wherein the same can be utilized for administering a vapor of an aromatic substance to a child having trouble breathing.

The general purpose of the present invention, which will be described subsequently in greater detail, is to provide a new infant breathing aid assembly apparatus and method which has many of the advantages of the pacifiers mentioned heretofore and many novel features that result in a new infant breathing aid assembly which is not anticipated, rendered obvious, suggested, or even implied by any of the prior art pacifiers, either alone or in any combination thereof.

To attain this, the present invention generally comprises an oral member for placing in the mouth of the infant. A first end of the oral member has a chamber extending therein toward the second end of the oral member. A face shield is provided for preventing the oral member from being swallowed by the infant. The face shield is preferably mounted on the oral member and positioned generally between the first end of the oral member and the face shield. A vapor emitter is provided that is removably insertable in the chamber of the oral member. The vapor emitter preferably comprises an absorbent member for absorbing an aromatic material. A cover is provided for covering the chamber and allowing passage of the vapors from the absorbent member out of the chamber. The cover is releasably attachable to the first end of the oral member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new infant breathing aid assembly apparatus and method which has many of the advantages of the pacifiers mentioned heretofore and many novel features that result in a new infant breathing aid assembly which is not anticipated, rendered obvious, suggested, or even implied by any of the prior art pacifiers, either alone or in any combination thereof.

It is another object of the present invention to provide a new infant breathing aid assembly which may be easily and efficiently manufactured and marketed.

It is a further object of the present invention to provide a new infant breathing aid assembly which is of a durable and reliable construction.

An even further object of the present invention is to provide a new infant breathing aid assembly which is susceptible of a low cost of manufacture with regard to both materials and labor, and which accordingly is then susceptible of low prices of sale to the consuming public, thereby making such infant breathing aid assembly economically available to the buying public.

Still yet another object of the present invention is to provide a new infant breathing aid assembly which provides in the apparatuses and methods of the prior art some of the advantages thereof, while simultaneously overcoming some of the disadvantages normally associated therewith.

Still another object of the present invention is to provide a new infant breathing aid assembly for administering a vapor of an aromatic substance to a child having trouble breathing.

Yet another object of the present invention is to provide a new infant breathing aid assembly which includes an oral member for placing in the mouth of the infant. A first end of the oral member has a chamber extending therein toward the second end of the oral member. A face shield is provided for preventing the oral member from being swallowed by the infant. The face shield is preferably mounted on the oral member and positioned generally between the first end of the oral member and the face shield. A vapor emitter is provided that is removably insertable in the chamber of the oral member. The vapor emitter preferably, comprises an absorbent member for absorbing an aromatic material. A cover is provided for covering the chamber and allowing passage of the vapors from the absorbent member out of the chamber. The cover is releasably attachable to the first end of the oral member.

Still yet another object of the present invention is to provide a new infant breathing aid assembly that provides parents and care givers an easier and safer way of administering medications, such as rubs, that are intended to be inhaled by an infant or a child. The present invention provides a chamber for holding the medication away from the child who could possible ingest the medication and become ill.

Even still another object of the present invention is to provide a new infant breathing aid assembly that can be used as a means of administering aromatherapy. Oils having relaxing fragrances may be used with the present invention to relax and calm an infant or toddler.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic perspective view of the present invention showing a locking member having a tapering portion, a blocking portion and a linking portion being formed on the oral member.

FIG. 4 is a schematic cross-sectional view of the present invention taken along line 3—3 of FIG. 1, showing an vapor emitter being positioned in the cavity of the oral member.

FIG. 5 is a schematic perspective view of the present invention showing a disk having an absorbent member attached thereto.

DESCRIPTION OF THE PREFERRED EMBODIMENT

Figure 1:
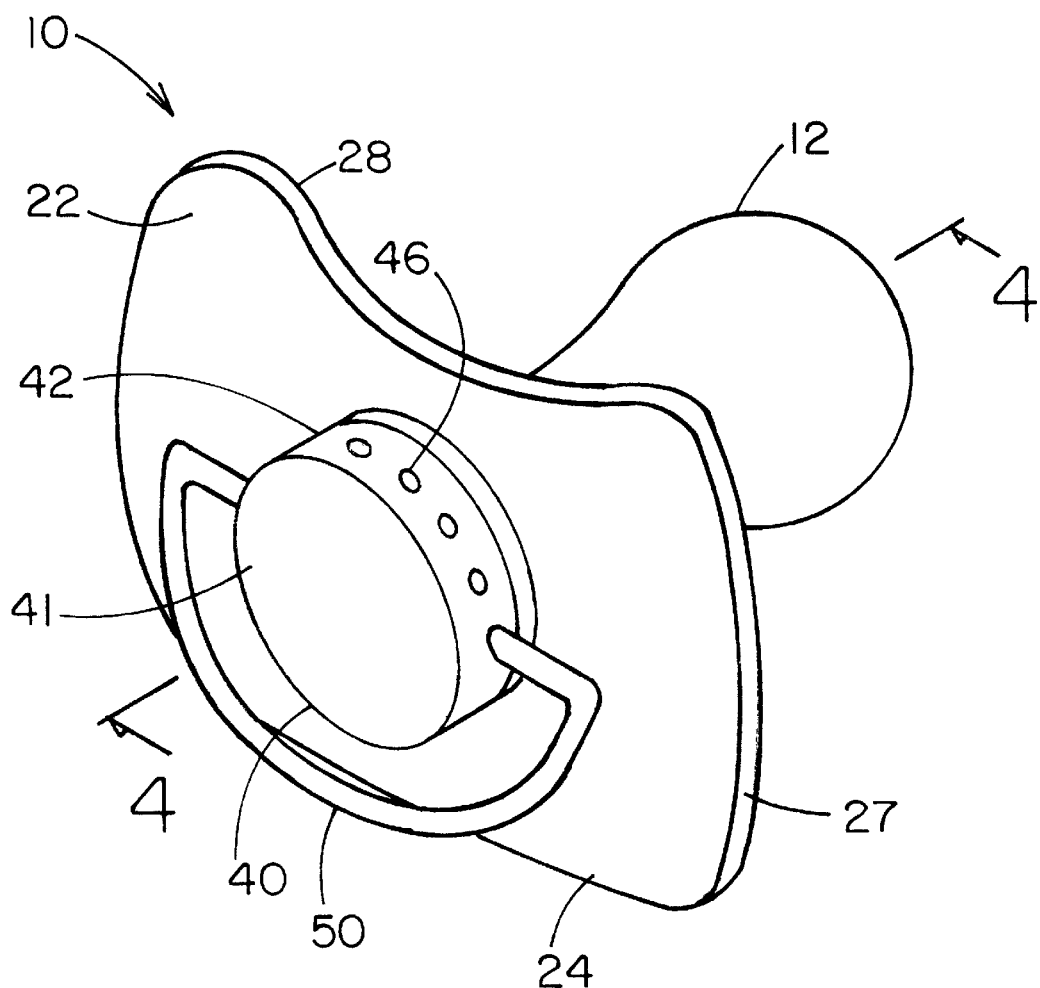
FIG. 1 is a schematic perspective view of a new infant breathing aid assembly according to the present invention showing a cover having a plurality of holes extending therein.
Figure 2:
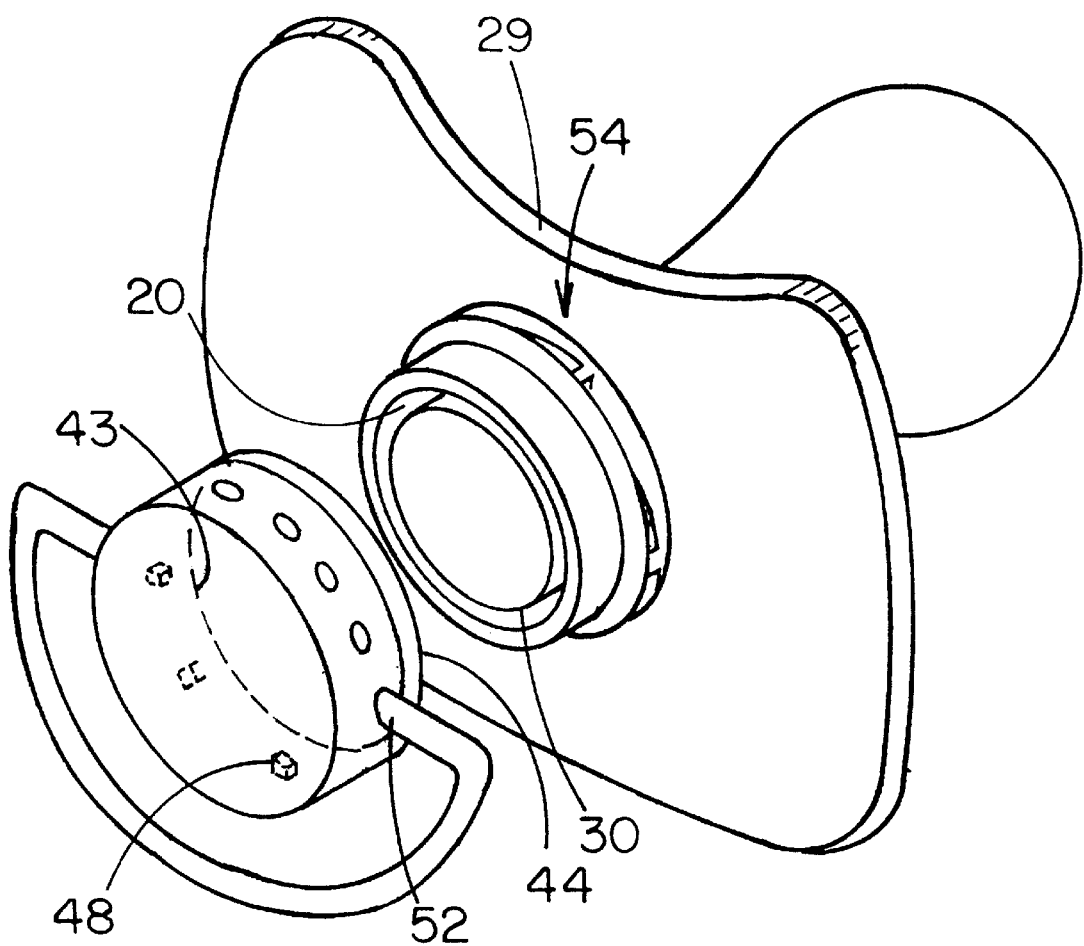
FIG. 2 is a schematic perspective view of the present invention showing the cover disengaged from the oral member showing a chamber extending into the oral member.

With reference now to the drawings, and in particular to FIGS. 1 through 5 thereof, a new infant breathing aid assembly embodying the principles and concepts of the present invention and generally designated by the reference numeral 10 will be described.

As best illustrated in FIGS. 1 through 5, the infant breathing aid assembly 10 generally comprises an oral member 12 for placing in the mouth of an infant. The oral member 12 has a first end 14 and a second end 16. The first end 14 of the oral member 12 has a chamber 20 extending therein toward the second end 16 of the oral member 12. The second end 16 of the oral member 12 preferably has a generally bulbous shape. The oral member 12 may comprise a resiliently flexible material, such as, for example, a rubber material.

A face shield 22 is provided for preventing the oral member 12 from being swallowed by the infant. The face shield 22 is mounted on the oral member 12 and preferably positioned generally adjacent to the first end 14 thereof. The face shield 22 is attached to a portion of the oral member 12 positioned generally between said first end 14 and said second end 16 of said oral member 12. The face shield 22 preferably comprises a plate 24 that has a front surface 25, a back surface 26, and a perimeter edge 27 extending between the front 25 and back surfaces 26. The front surface 25 preferably has a generally concave shape for selectively abutting a mouth of the infant. An upper portion 28 of the perimeter edge 27 may have a depression 29 extending therein for allowing a nose of the infant pass by the plate 24. The face shield 22 may comprise a substantially rigid material such as, for example, a plastic material.

A vapor emitter 30 is provided that is removably insertable in the chamber 20 of the oral member 12. The vapor emitter 30 preferably comprises a disk 31 that has a front surface 32 and a back surface 33. The back surface 33 selectively abuts a bottom wall 34 of the chamber 20. An absorbent member 36 is provided for absorbing an aromatic material. The absorbent member 36 is preferably attached to and generally covering the front surface 32 of the disk 31. The absorbent member 36 may comprise an absorbent material such as, for example, a cotton or a cloth material.

A cover 40 is provided for covering the chamber 20 and allowing passage of the vapors from the vapor emitter 30 out of the chamber 20. The cover 40 preferably comprises a plate 41. The plate 41 of the cover 40 has a peripheral wall 42 extending upwardly away from the plate 41. A free edge 43 of the peripheral wall 42 defines an opening 44 extending into a cavity 45 of the cover 40. The peripheral wall 42 has a plurality of holes 46 extending therethrough for allowing fluid communication between the vapor emitter 30 and a nostril of the infant. Each of the holes 46 of the peripheral wall 42 is spaced apart from each other allowing for even disbursement of the vapors. An inner surface 47 of the peripheral wall 42 has a plurality of protruding members 48 extending away therefrom. In one embodiment, the first end 14 of the oral member 12 is preferably positionable in the cavity 45 of the cover 40. The cover 40 may comprise a generally circular shape. However, the cover 40 may also comprise a variety of other shapes such as, for example, a rectangular or an oval shape.

A handle 50 may be mounted on the cover 40. The handle 50 preferably comprises an arcuate member that has a pair of ends 52. Each of the ends 52 is preferably pivotally attached to the peripheral wall 42 of the cover 40. The arcuate member may comprise a substantially rigid material such as, for example, a plastic material.

A plurality of locking members 54 may be provided for locking the cover 40 to the oral member 12. Each of the locking members 54 is formed on the oral member 12. Each of the locking members 54 preferably comprises a tapering portion 55 that has a first end 56 and a second end 57. A first side surface 58 of the tapering portion 55 tapers from the first end 56 toward the second end 57. The tapering portion 55 is positioned generally between the first end 14 of the oral member 12 and the face shield 24.

Each of the locking members 54 also preferably include a blocking portion 60 that has a first end 61 and a second end 62. The blocking portion 60 has a longitudinal axis that is orientated generally perpendicular to a plane extending between the ends of the tapering portion 55. The blocking portion 60. is positioned generally next to the first end 56 of the tapering portion 55.

A linking portion 64 is provided for linking the blocking portion 60 to the tapering portion 55. The linking portion 64 extends between the first end 61 of the blocking portion 60 and the first end 56 of the tapering portion 55 and coupled thereto. A distance between the blocking portion 60, the linking portion 64 and the tapering portion 55 defines a recess portion 66.

In use, one of the protruding members 48 of the cover 40 selectively moves along the first side surface 58 of the tapering portion 55 and selectively engages the recess portion 66. The blocking portion 60 keeps the protruding member 48 in the recess portion 66. In one embodiment, a user must push downwardly upon the cover to extract the protruding member 48 from the recess portion 66 and remove the cover 40 from the oral member 12.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An infant breathing aid assembly that is adapted for being removably inserted in a mouth of an infant, said assembly comprising:

an oral member for placing in the mouth of the infant, a first end of said oral member having a chamber extending therein toward a second end of said oral member;

a plurality of locking members being formed on an outer surface of said oral member;

a face shield for preventing said oral member from being swallowed by the infant, said face shield being mounted on said oral member and positioned generally adjacent to said first end thereof;

a vapor emitter for emitting vapors being removably insertable in said chamber of said oral member, said vapor emitter including an absorbent member for absorbing an aromatic material;

a cover for covering said chamber being releasably attachable to said first end of said oral member, said cover comprising a plate and a peripheral wall being mounted to said plate and extending away from said plate;

a plurality of protruding members being mounted to and extending away from an inner surface of said peripheral wall of said cover, each of said protruding members being selectively engagable with a respective one of said plurality of said locking members when said cover is attached to said first end of said oral member such that said cover is selectively lockable on said oral member to restrict the infant from accessing said vapor emitter; and said vapor emitter including a disk having a front surface and a back surface, said back surface selectively abutting a bottom wall of said chamber, said absorbent member being attached to and generally covering said front surface of said disk.

2. The infant breathing aid assembly of claim 1, wherein said second end of said oral member has a generally bulbous shape.

3. The infant breathing aid assembly of claim 1, wherein said face shield comprises a plate having a perimeter edge extending between a front and a back surface, an upper portion of said perimeter edge having a depression extending therein.

4. The infant breathing aid assembly of claim 3, wherein said front surface has a generally concave shape.

5. The infant breathing aid assembly of claim 1, wherein a free edge of said peripheral wall defines an opening extending into a cavity of said cover; and said peripheral wall having a plurality of holes extending therethrough for allowing passage of the vapors from said absorbent member out of said chamber.

6. The infant breathing aid assembly of claim 1, wherein each of said locking member comprises:

a tapering portion having a first end and a second end, a first side surface of said tapering portion tapering from said first end toward said second end;

a blocking portion having a first end and a second, said blocking member being positioned generally next to said first end of said tapering portion; and a linking portion for linking said blocking portion to said tapering portion, said linking portion extending between said first end of said blocking portion and said first end of said linking portion and coupled thereto.

7. The infant breathing aid assembly of claim 6, wherein a distance between said blocking portion, said linking portion and said tapering portion defines a recess portion;

wherein each of said protruding members of said cover is selectively positionable along a length of said first side surface of said tapering portion of a corresponding one of said locking members as said cover is rotated about said first end of said oral member until each of said protruding members is positioned in a corresponding recess portion; and wherein said cover is selectively releasable from said oral member when said cover is biased towards said face shield thereby positioning each of said protruding members out of respective said recesses while simultaneously being rotated about said first end of said oral member until each of said protruding members is unobstructed by respective said locking members.

8. The infant breathing aid assembly of claim 1, additionally comprising:
   a handle mounted on said cover.

9. The infant breathing aid assembly of claim herein said handle comprises an arcuate member having a pair of ends, each of said ends being pivotally attached to said peripheral wall of said cover.

10. The infant breathing aid assembly of claim 1, wherein the peripheral wall of said cover has a plurality of holes for permitting vapors emitted by the vapor emitter to escape from said cover, said hole in said peripheral wall being confined to one semicircular half of said peripheral wall.

11. An infant breathing aid assembly that is adapted for being removably inserted in a mouth of an infant, said assembly comprising:
   an oral member for placing in the mouth of the infant, said oral member having a first end and a second end, said first end of said oral member having a chamber extending therein toward said second end of said oral member, said second end of said oral member having a generally bulbous shape, said oral member comprising a resiliently flexible material;
   a face shield for preventing said oral member from being swallowed by the infant, said face shield being mounted on said oral member and positioned generally adjacent to said first end thereof, said face shield comprising:
      a plate having a front surface, a back surface, and a perimeter edge extending between said front and back surfaces, said front surface having a generally concave shape, an upper portion of said perimeter edge having a depression extending therein, said face shield comprising a substantially rigid material;
   a vapor emitter for emitting vapors being removably insertable in said chamber of said oral member, said vapor emitter comprising:
      a disk having a front surface and a back surface, said back surface selectively abutting a bottom wall of said chamber;
      an absorbent member for absorbing a decongestant material, said absorbent member being attached to and generally covering said front surface of said disk, said absorbent member comprising an absorbent material;
   a cover for covering said chamber and allowing passage of the vapors from said vapor emitter out of said chamber, said cover comprising:
      a plate and a peripheral wall being mounted to said plate and extending away from said plate, a free edge of said peripheral wall defining an opening extending into a cavity of said cover;
      said peripheral wall having a plurality of holes extending therethrough for allowing fluid communication between said vapor emitter and a nostril of the infant, each of said holes of said peripheral wall being spaced apart from each other;
      an inner surface of said peripheral wall having a plurality of protruding members, each of said protruding members being positioned generally adjacent to said free edge of said peripheral wall of said cover; said first end of said oral member being positionable in said cavity of said cover;
   a handle mounted on said cover, said handle comprising an arcuate member, said arcuate member having a pair of ends, each of said ends being pivotally attached to said peripheral wall of said cover, said arcuate member comprising a substantially rigid material; and
   a plurality of locking members for locking said cover to said oral member, each of said locking members being formed on said oral member, each of said locking members comprising:
      a tapering portion having a first end and a second end, a first side surface of said tapering portion tapering from said first end toward said second end, a second side surface of said tapering portion extending between said first and second ends of said tapering portion, said tapering portion being positioned generally between said first end of said oral member and said face shield;
      a blocking portion having a first end and a second, said blocking portion having a longitudinal axis being orientated generally perpendicular to a plane of said second side surface of said tapering portion, said blocking portion being positioned generally next to said first end of said tapering portion;
      a linking portion for linking said blocking portion to said tapering portion, said linking portion extending between said first end of said blocking portion and said first end of said linking portion and coupled thereto, a distance between said blocking portion, said linking portion and said tapering portion defining a recess portion; and
   each of said protruding members being selectively engagable with a respective one of said plurality of said locking members when said cover is attached to said first end of said oral member such that said cover is selectively lockable on said oral member to restrict the infant from accessing said vapor emitter;
   wherein each of said protruding members of said cover is selectively positionable along a length of said first side surface of said tapering portion of a corresponding one of said locking members as said cover is rotated about said first end of said oral member until each of said protruding members is positioned in a corresponding recess portion; and
   wherein said cover is selectively releasable from said oral member when said cover is biased towards said face shield thereby positioning each of said protruding members out of respective said recesses while simultaneously being rotated about said first end of said oral member until each of said protruding members is unobstructed by respective said locking members.

12. An infant breathing aid assembly that is adapted for being removably inserted in a mouth of an infant, said assembly comprising:
   an oral member for placing in the mouth of the infant, a first end of said oral member having a chamber extending therein toward a second end of said oral member;
   a plurality of locking members being formed on an outer surface of said oral member;
   a face shield for preventing said oral member from being swallowed by the infant, said face shield being mounted on said oral member and positioned generally adjacent to said first end thereof;
   a vapor emitter for emitting vapors being removably insertable in said chamber of said oral member, said vapor emitter including an absorbent member for absorbing an aromatic material;

a cover for covering said chamber being releasably attachable to said first end of said oral member, said cover comprising a plate and a peripheral wall being mounted to said plate and extending away from said plate;

a plurality of protruding members being mounted to and extending away from an inner surface of said peripheral wall of said cover, each of said protruding members being selectively engagable with a respective one of said plurality of said locking members when said cover is attached to said first end of said oral member such that said cover is selectively lockable on said oral member to restrict the infant from accessing said vapor emitter;

said vapor emitter including a disk having a front surface and a back surface, said back surface selectively abutting a bottom wall of said chamber, said absorbent member being attached to and generally covering said front surface of said disk;

each of said locking member comprising:
  a tapering portion having a first end and a second end, a first side surface of said tapering portion tapering from said first end toward said second end;
  a blocking portion having a first end and a second, said blocking member being positioned generally next to said first end of said tapering portion; and
  a linking portion for linking said blocking portion to said tapering portion, said linking portion extending between said first end of said blocking portion and said first end of said linking portion and coupled thereto.

13. The infant breathing aid assembly of claim 12, wherein said second end of said oral member has a generally bulbous shape.

14. The infant breathing aid assembly of claim 12, wherein said face shield comprises a plate having a perimeter edge extending between a front and a back surface, an upper portion of said perimeter edge having a depression extending therein.

15. The infant breathing aid assembly of claim 14, wherein said front surface has a generally concave shape.

16. The infant breathing aid assembly of claim 12, wherein a free edge of said peripheral wall defines an opening extending into a cavity of said cover; and
  said peripheral wall having a plurality of holes extending therethrough for allowing passage of the vapors from said absorbent member out of said chamber.

17. The infant breathing aid assembly of claim 12, wherein a distance between said blocking portion, said linking portion and said tapering portion defines a recess portion;
  wherein each of said protruding members of said cover is selectively positionable along a length of said first side surface of said tapering portion of a corresponding one of said locking members as said cover is rotated about said first end of said oral member until each of said protruding members is positioned in a corresponding recess portion; and
  wherein said cover is selectively releasable from said oral member when said cover is biased towards said face shield thereby positioning each of said protruding members out of respective said recesses while simultaneously being rotated about said first end of said oral member until each of said protruding members is unobstructed by respective said locking members.

18. The infant breathing aid assembly of claim 12, additionally comprising:
  a handle mounted on said cover.

19. The infant breathing aid assembly of claim 18, wherein said handle comprises an arcuate member having a pair of ends, each of said ends being pivotally attached to said peripheral wall of said cover.

20. The infant breathing aid assembly of claim 12, wherein the peripheral wall of said cover has a plurality of holes for permitting vapors emitted by the vapor emitter to escape from said cover, said hole in said peripheral wall being confined to one semicircular half of said peripheral wall.

* * * * *